US008588268B2

(12) United States Patent
Boutoussov et al.

(10) Patent No.: US 8,588,268 B2
(45) Date of Patent: *Nov. 19, 2013

(54) HIGH POWER RADIATION SOURCE WITH ACTIVE-MEDIA HOUSING

(75) Inventors: Dmitri Boutoussov, Dana Point, CA (US); Vladimir S. Netchitailo, Irvine, CA (US)

(73) Assignee: Biolase, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/912,680

(22) Filed: Oct. 26, 2010

(65) Prior Publication Data

US 2011/0096802 A1  Apr. 28, 2011

Related U.S. Application Data

(60) Provisional application No. 61/255,031, filed on Oct. 26, 2009, provisional application No. 61/261,745, filed on Nov. 16, 2009, provisional application No. 61/321,041, filed on Apr. 5, 2010, provisional application No. 61/383,227, filed on Sep. 15, 2010.

(51) Int. Cl.
*H01S 3/08* (2006.01)

(52) U.S. Cl.
USPC .............. 372/92; 372/36; 372/66; 372/70; 372/71; 372/72; 372/87

(58) Field of Classification Search
USPC ............ 372/36, 66, 70–72, 87, 92; 606/17
See application file for complete search history.

(56) References Cited

U.S. PATENT DOCUMENTS

| 4,122,853 A | 10/1978 | Smith |
| 4,858,242 A | 8/1989 | Kuper et al. |
| 5,210,768 A * | 5/1993 | Seguin .......................... 372/92 |
| 5,246,436 A * | 9/1993 | Rowe ............................ 606/13 |

(Continued)

FOREIGN PATENT DOCUMENTS

| JP | 48-95792 | 3/1973 |
| JP | 52-046795 | 4/1977 |

(Continued)

OTHER PUBLICATIONS

International Search Report and Written Opinion, PCT/US2010/054161, mailed Jan. 4, 2011.

(Continued)

*Primary Examiner* — Yuanda Zhang
(74) *Attorney, Agent, or Firm* — Jones Day

(57) ABSTRACT

A high power source of electro-magnetic radiation having a multi-purpose housing is disclosed. The multi-purpose housing includes an interior filled with a material forming at least a light source and further comprising a reflector which can envelope a laser rod surrounded by light sources for providing light excitation to the laser rod. A material defining outer surfaces of the light sources extends out to and defines outer surfaces of the reflector. A high-reflectivity coating is disposed over an outer surface of the reflector, as is a protective coating. Also disposed over an outer surface of the reflector can be an optional heat sink, with cooling being performed by an optional arrangement of forced-air traveling over the heat sink. The light sources may be light source pumps, and the high-reflectivity coating may be formed to envelop the reflector.

20 Claims, 13 Drawing Sheets

(56) References Cited

U.S. PATENT DOCUMENTS

| | | | |
|---|---|---|---|
| 5,351,251 A * | 9/1994 | Hodgson | 372/4 |
| 5,434,880 A * | 7/1995 | Burrows et al. | 372/69 |
| 5,646,674 A * | 7/1997 | Bacon et al. | 347/257 |
| 5,651,783 A * | 7/1997 | Reynard | 606/4 |
| 5,708,675 A * | 1/1998 | Moon et al. | 372/92 |
| 5,802,086 A | 9/1998 | Hargis et al. | |
| 6,026,102 A * | 2/2000 | Shimoji | 372/22 |
| 6,327,291 B1 | 12/2001 | Marshall | |
| 2002/0182563 A1 | 12/2002 | Boutoussov et al. | |
| 2006/0029120 A1 | 2/2006 | Mooradian et al. | |
| 2007/0100330 A1 | 5/2007 | Tilleman | |
| 2008/0203280 A1 | 8/2008 | Rizoiu et al. | |
| 2009/0129425 A1 * | 5/2009 | Petrescu-Prahova | 372/66 |

FOREIGN PATENT DOCUMENTS

| | | |
|---|---|---|
| JP | 2001-068768 | 3/2001 |
| JP | 2008-091486 | 4/2008 |
| JP | 2005-217281 | 8/2008 |
| JP | 2009-010066 | 1/2009 |
| WO | 2011053604 | 5/2011 |

OTHER PUBLICATIONS

International Search Report and Written Opinion, PCT/US2011/051716, Jan. 10, 2012.

Notice of Preliminary Rejection issued on Jul. 25, 2013 in the related/corresponding Korean Patent Appl. No. 10-2012-7013195, entitled, "High Power Radiation Source with Active-Media Housing," (9 pages).

Office Action issued on Aug. 5, 2013 in the related/corresponding Japanese Patent Appl. No. 2012-535459, entitled, "High Power Radiation Source with Active-Media Housing," (8 pages).

International Preliminary Report on Patentability from related/corresponding International Application No. PCT/US10/54161 filed Oct. 26, 2010 (4 pages).

* cited by examiner

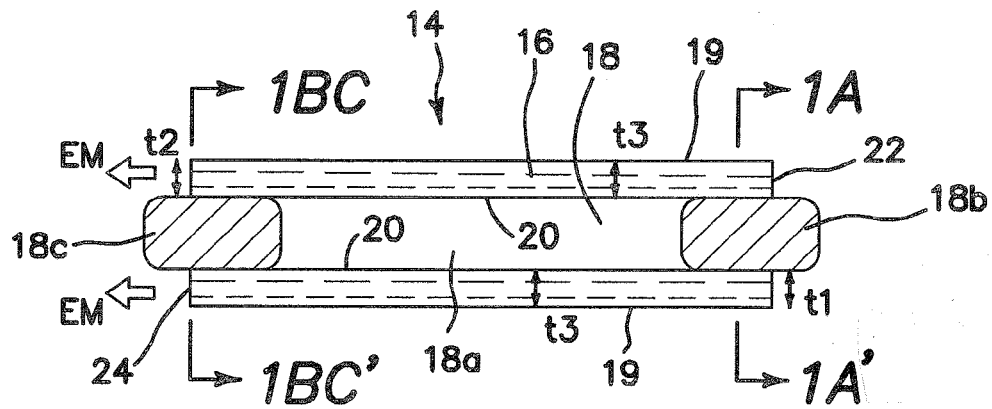
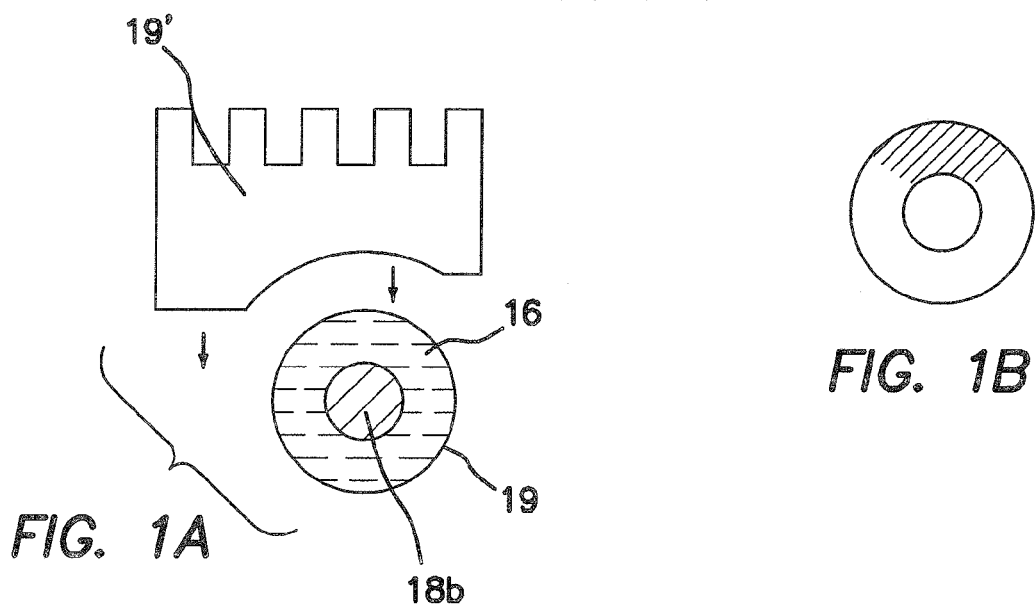
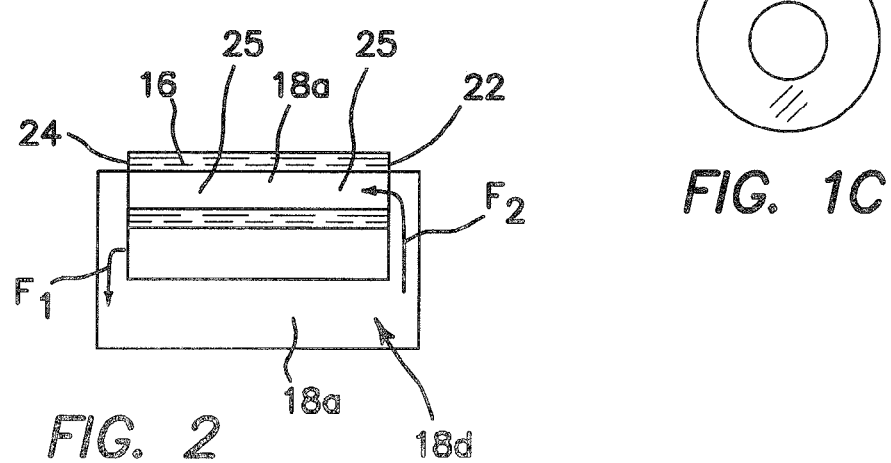

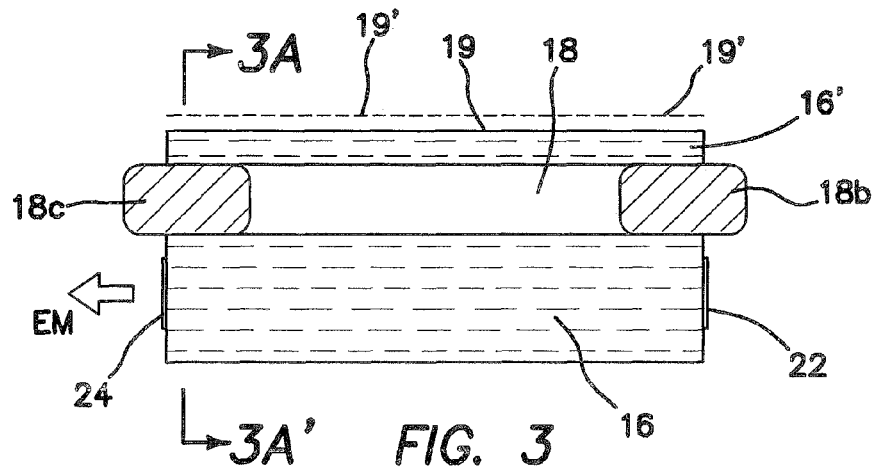
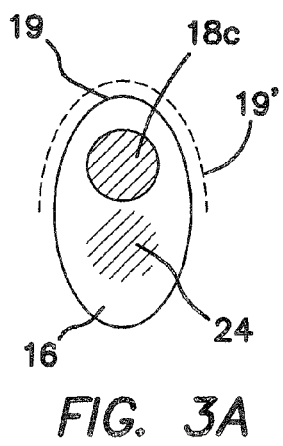
FIG. 3A
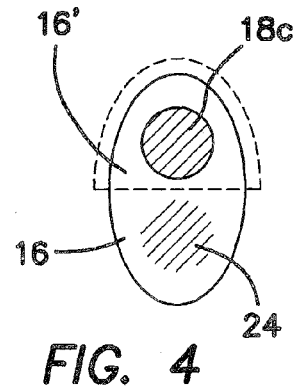
FIG. 4
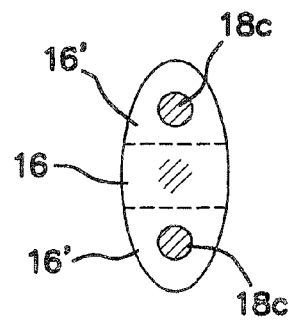
FIG. 5
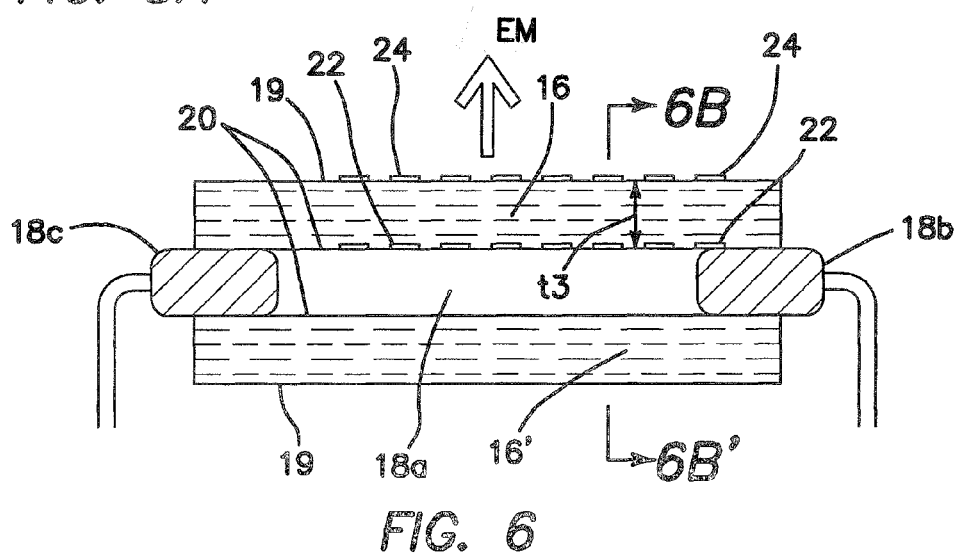
FIG. 6

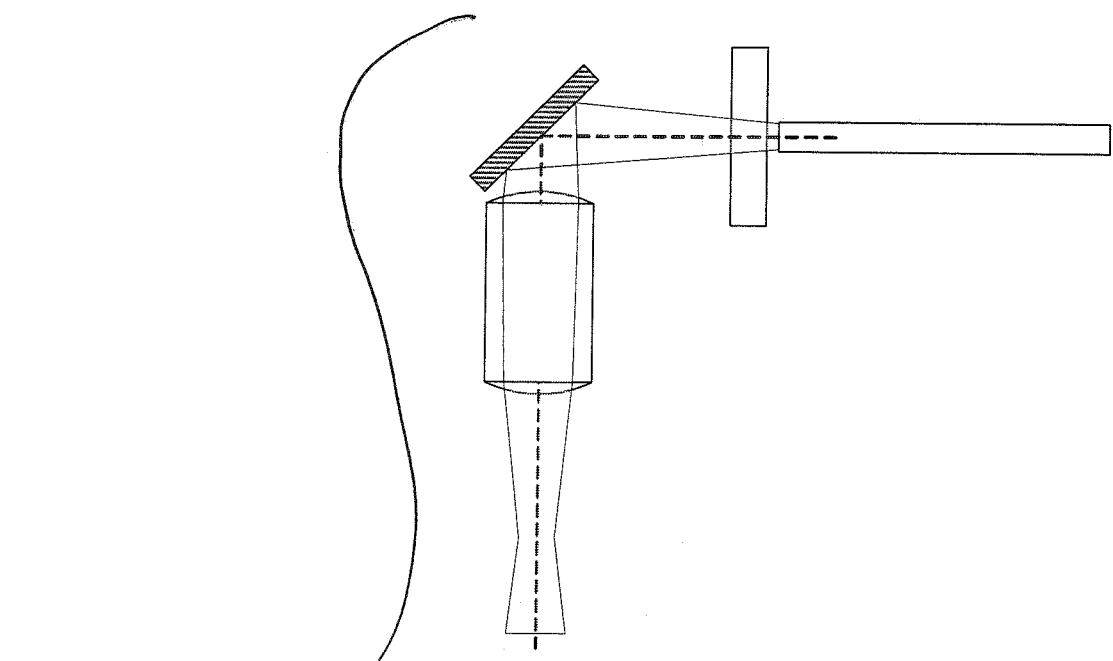
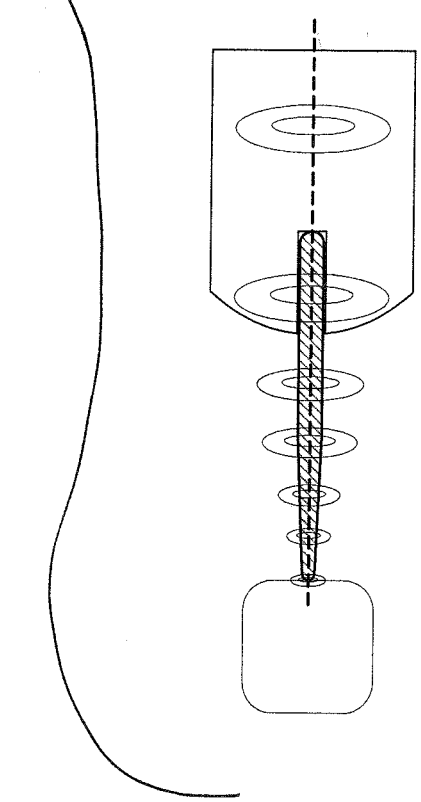
FIG. 15

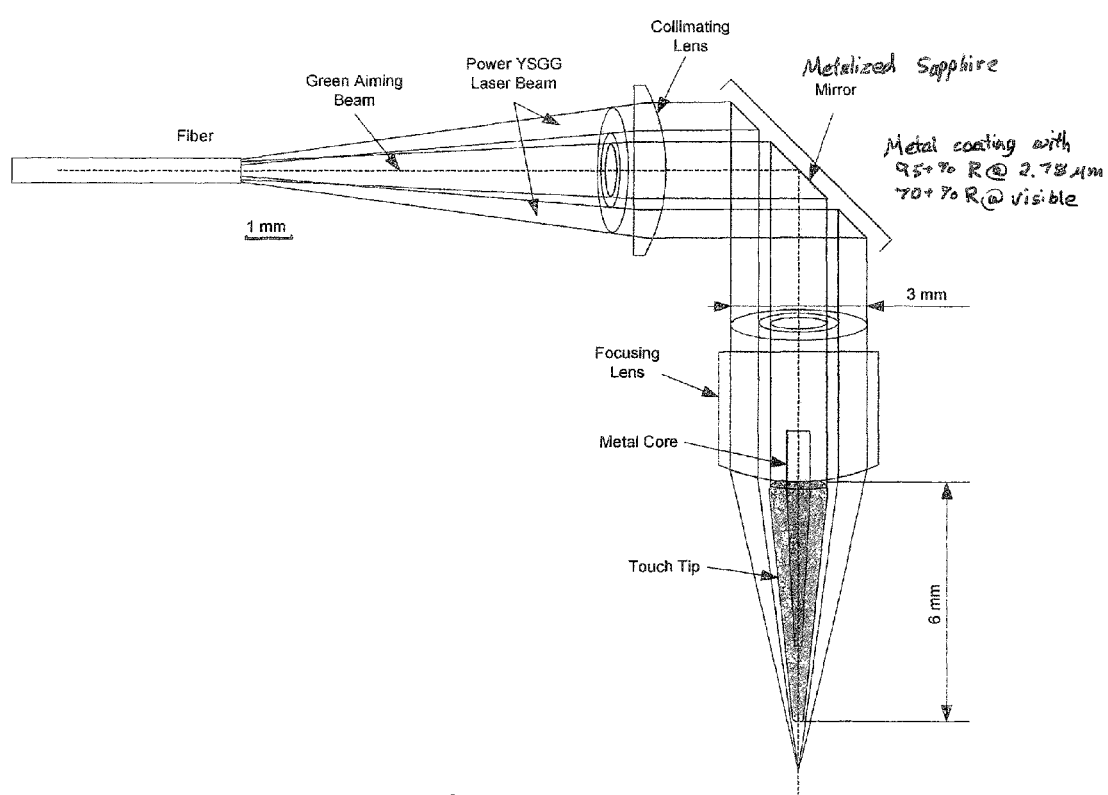

US 8,588,268 B2

HIGH POWER RADIATION SOURCE WITH ACTIVE-MEDIA HOUSING

CROSS-REFERENCE TO RELATED APPLICATIONS

This application claims the benefit of Prov. App. 61/255,031, filed Oct. 26, 2009 and entitled HIGH POWER RADIATION SOURCE WITH ACTIVE-MEDIA HOUSING, Prov. App. 61/261,745, filed Nov. 16, 2009 and entitled HIGH POWER RADIATION SOURCE WITH ACTIVE-MEDIA HOUSING, Prov. App. 61/321,041, filed Apr. 5, 2010 and entitled TOUCH-TIP FOR MEDICAL LASER, and Prov. App. 61/383,227, filed Sep. 15, 2010 and entitled HIGH POWER SOURCE OF ELECTROMAGNETIC RADIATION, the content all of which are expressly incorporated herein by reference.

This application relates to Prov. App. 61/252,552, filed Oct. 16, 2009 and entitled HIGH POWER SOURCE OF ELECTROMAGNETIC RADIATION, Prov. App. 61/221,544, filed Jun. 29, 2009 and entitled AIR COOLED SOLID STATE LASER, and application Ser. No. 12/363,679, entitled COATED DIFFUSIVE TYPE REFLECTOR FOR SOLID STATE FLASH LAMP PUMP LASER, which claims priority to Prov. App. 61/025,398, the contents of all which are expressly incorporated herein by reference.

This invention also relates to U.S. Pat. No. 7,108,693, entitled ELECTROMAGNETIC ENERGY DISTRIBUTIONS FOR ELECTROMAGNETICALLY INDUCED MECHANICAL CUTTING, application Ser. No. 11/330,388, entitled FLUID CONDITIONING SYSTEM, and U.S. Pat. No. 5,741,247, entitled USER PROGRAMMABLE COMBINATION OF ATOMIZED PARTICLES FOR ELECTROMAGNETICALLY INDUCED CUTTING, all the contents of which are expressly incorporated herein by reference.

BACKGROUND OF THE INVENTION

1. Field of the Invention

The present invention relates generally to radiation outputting devices and, more particularly, to devices that emit, reflect or channel radiation.

2. Description of Related Art

A variety of radiation outputting systems have existed in the prior art, each offering its own sundry advantages and commensurate shortcomings. In the context of optical systems, the laser has no doubt received much attention and developmental effort going almost as far back in time as the advent of the coherent-energy emitting device itself. For example, relatively complex systems such as that for emitting a ring-shaped laser beam for use with fluids in the context of medical and dental applications were disclosed over a quarter century ago by Muncheryan as evidenced in U.S. Pat. No. 3,821,510. More recently, highly-effective medical and dental laser procedural devices have been revealed in U.S. Pat. No. 5,741,247 capable of focusing energy into a mist of water above a target resulting in cutting or ablating of the target by one or more of the water, the energy, and shock waves. Such procedural devices when embodied by solid state lasers, for instance, can be advantageous in that they are compact, reliable for long-term use, and easily replaced in the field.

SUMMARY OF THE INVENTION

An embodiment of the present invention can take the form of a multi-functional housing, which may comprise and/or contain a laser rod, a hole formed (e.g., drilled) along/through a longitudinal axis of the laser rod to hollow-out a portion thereof, a longitudinal lumen formed within the laser rod as a consequence of the drilling and hollowing, and a flashlamp disposed at least in part inside the longitudinal lumen along a length thereof. Reflectors (e.g., HR and/or OC) facilitating pumping of a developing laser beam within the longitudinal lumen can be provided, for example, in any of a variety of sundry shapes. Circular-perimeter shaped reflectors may be of particular benefit for coupling of the emitted light to fiber(s). A reflector, additionally or alternatively, can be disposed around part or all of the outside of the laser rod, or not. When HR and OC mirrors are used, they can be placed at opposing ends of the laser rod such as to provide functionality in the shape of, for instance, donut shaped mirrors suitable for effectuating generation of a donut-shaped radiation pattern).

Embodiments can have anodes to fire flashlamp(s), and/or can have RF pumping (or some other type such as diode side-pumping) wherein for instance anodes/cathodes are not provided and/or provision may be made to circulate (but not necessarily re-circulate) the interior (e.g., with Xenon gas) of the laser rod. Preferably, cooling structure (e.g., any one or more of the below referenced structures including, e.g., heat sinks) is disposed on the outside (e.g., attached to the crystal of the laser rod). Such can be air and/or water cooling.

A reflector according to the present invention is made to include the shape (e.g., body) of one or more radiation sources (e.g., light sources) that provide driving energy (e.g., light) causing the reflector to output radiation (i.e., electromagnetic energy). A material defining outer surfaces of the light sources extends out to and defines outer surfaces of the reflector, too. A high-reflectivity coating can be disposed over an outer surface of the reflector, followed by an optional protective coating. Also, a heat sink can be coupled to the reflector with cooling taking place by way of the directing of forced-air over parts of the heat sink.

By way of example only and not limitation, in the context of an optical system, the reflector can be for a pumping-chamber which optionally may be air cooled, and can include (e.g., as an integral part thereof) a gain medium (e.g., laser rod) next to one or surrounded by a plurality of stimulation sources (e.g., light sources) that provide driving energy (e.g., light excitation) to the gain medium causing the gain medium to output electromagnetic energy. Each stimulation source may be a light source pump, and the high-reflectivity coating may be formed to envelop the reflector.

In one aspect, a high power source of electro-magnetic radiation has a multi-purpose housing which comprises an interior filled with a material forming at least a light source and further comprises a reflector which can envelope (optionally) a laser rod surrounded by light sources for providing light excitation to the laser rod.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE FIGURES

FIG. 1 shows a side cross-sectional view of a multi-functional housing according to an embodiment of the present invention;

FIG. 1A shows an end cross-sectional view of the same embodiment along with an optional cooling implement;

FIGS. 1B and 1C show end cross-sectional views of the same embodiment;

FIG. 2 shows a side cross-sectional view of a multi-functional housing according to a fluid-cooled alternative embodiment of the present invention;

FIG. 3 shows a side cross-sectional view of a multi-functional housing according to an asymmetrical-type alternative embodiment of the present invention;

FIG. 3A shows an end cross-sectional view of the asymmetrical-type embodiment, along with an optional reflector implement;

FIG. 4 shows a modified version of the asymmetrical-type embodiment of FIGS. 3 and 3A, along with an optional reflector implement;

FIG. 5 shows yet another modified version of the asymmetrical-type embodiment of FIGS. 3 and 3A, along with an optional reflector implement;

FIG. 6 shows a side cross-sectional view of a multi-functional housing according to an transverse-pumping arrangement of the present invention;

FIGS. 11-18 show further aspects of the present invention.

DETAILED DESCRIPTION OF THE INVENTION

Figure 6A:
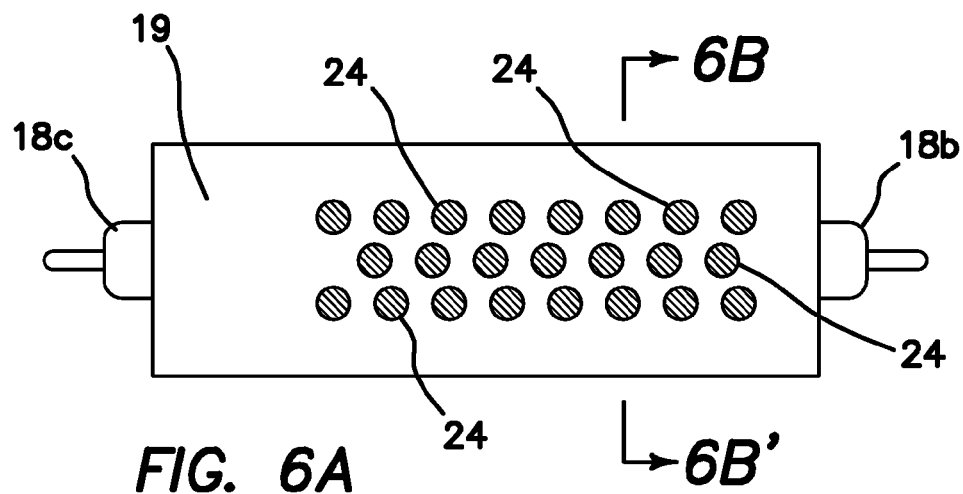
FIG. 6A shows a top plan view of the transverse-pumping arrangement.

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various devices and techniques that are conventionally used in the art, and only so much of the commonly practiced process steps are included herein as are necessary to provide an understanding of the present invention. The present invention has applicability in the field of radiation outputting systems and processes in general, such as devices (e.g., LEDs, headlamps, etc.) that emit, reflect or channel radiation.

Referring more particularly to the drawings a multi-functional housing 14 according to the present invention is depicted in FIG. 1 by way of a side cross-sectional rendition of the multi-functional housing 14, according to an embodiment of the present invention. The multi-functional housing 14 comprises an active media 16 and an interior excitation region 18. The interior excitation region 18 may be, contain, comprise, or provide a function of an excitation source to the active media 16. For instance, the interior excitation region 18 may be provided to function as a flashlamp. According to such arrangements, the active media 16 typically may comprise a laser rod, such as a modified laser rod. With reference to arrangements, such as for instance that of the depicted embodiment, a method of constructing the multi-function housing 14 can comprise, for example, providing a laser rod, and forming (e.g., drilling) a hole along/through (e.g., to hollow out) its longitudinal axis, whereby the remaining part of the laser rod forms the active media 16. In exemplary instances, performing the process can yield a cylindrically-shaped active media having an interior region suitable for accommodating an excitation source such as a flashlamp.

In further reference to the invention, such as elucidated in the illustrated embodiment of FIG. 1, an excitable fluid (e.g., a lamp gas 18a) may be provided in the interior excitation region 18. Additionally, in the depicted example, one or more energy conductors or electrodes (e.g., lamp electrodes 18b and 18c) can be provided at different vicinities (e.g., to encompass, such as at opposing ends) relative to (e.g. within) the interior excitation region 18.

According to an end-pumped implementation such as depicted in FIG. 1, components may be provided, for example, as optics (e.g., a High Reflector HR and/or an Output Coupler OC) at different vicinities (e.g., at opposing ends) relative to (e.g. within or at or near ends of) the active media 16, in any shape. FIG. 1A shows an end cross-sectional view of the embodiment of FIG. 1, taken along the line 1A-1A' of FIG. 1, and further shows an optional cooling implement 19'. Circular perimeters, such as defined by the exterior surface 19 of the active media 16 in FIG. 1A, may be of benefit for the coupling to fiber(s), e.g., which may also have circular cross sections. In certain embodiments, HR and OC mirrors (e.g., one or more of which may comprise coatings) can be placed at opposing ends of the active media 16 and/or can be formed to have "O" (e.g., washer) shapes for generating, for example, an "O" shaped radiation pattern. Other implementations may comprise other shapes of components (e.g., HRs and/or OCs) as exemplified in counterpart FIG. 1B (having an HR(s) and/or OC(s) only about one-quarter the size of the "O" shape, with of course other sizes, shapes and/or positions being possible) and 1C (having HRs and/or OCs smaller than the 1B depiction, such as one(s) having circular cross sections), with of course other sizes, shapes and/or positions being possible). Referring to those two figures FIG. 1B shows an end side view of the embodiment of FIG. 1, taken along the line 1BC-1BC' of FIG. 1, with FIG. 1C showing an end cross-sectional view of another alternative to the embodiment of FIG. 1 from the perspective again of the line 1BC-1BC' of FIG. 1. The cross-hatched areas represent the HR and/or OC component(s).

In a typical construction of the FIG. 1 arrangement, for instance, the components are embodied as a washer-shaped HR 22 and a washer-shaped OC 24 with thicknesses functionally suited (e.g., matching, corresponding to, and/or equaling) to one or more thicknesses of the active media 16 as measured, for example, between the exterior surface 19 and an interior surface 20. For instance, one or both of the thickness t1 of the HR and the thickness t2 of the OC may match, correspond to, or equal a thickness t3 of the laser rod. In the example of FIG. 1, t1=t2=t3. As indicated in FIG. 1, a reflector (which may comprise the curved surface of cooling implement 19', for example, and/or may comprise a membrane, layer, or coating with or without the cooling structure) may or may not be disposed around part or all of the outside of the active media 16 and/or the active media 16 may be formed to be sufficiently thick so that reflector(s) are not needed.

Embodiments can have electrodes (cf. 18b and 18c), for example, to fire, for instance, flashlamp(s) and/or can have RF pumping implements 25 (e.g., within and/or, preferably, external of part or all of 14) as depicted in FIG. 2 or some other type(s), such as diode side-pumping wherein for instance anodes/cathodes are not provided and/or provision may be made to circulate (but not necessarily re-circulate) the interior (e.g., with the lamp gas, such as Xenon, within a chamber 18d and driven in directions of the arrows f1 and f2). FIG. 2 shows a side cross-sectional view of a multi-functional housing according to a fluid-cooled alternative embodiment of the present invention. Preferably, cooling structure (e.g., any one or more of the below referenced structures including, e.g., heat sinks) and/or cooling implements 19' such as exemplified in FIG. 1A are also or alternatively used such as by way of being disposed on the outside (e.g., attached to the crystal of the active media 16). Such can be or achieve air and/or water cooling.

FIG. 3 shows a side cross-sectional view of a multi-functional housing according to an asymmetrical-type alternative embodiment of the present invention, and FIG. 3A shows an end cross-sectional view of the asymmetrical-type embodiment, taken along the line 3A-3A' of FIG. 3, along with an optional reflector and/or cooling implement (cf. cooling implement 19' of FIG. 1A). According to some implementations, the phantom line 19' in FIGS. 3 and 3A is a reflective surface disposed over or around the top half only; whereby some or all of the underlying media can be "inactive" media 16' (e.g., since the reflective surface 19' can direct it toward active (e.g., doped) parts 16 of the resonator and/or toward 22 and/or 24). Active media 16 regions and inactive media 16' regions may be defined by one or more of adjoining (e.g., molecular bonding) and/or doping. FIG. 4 shows a modified version of the asymmetrical-type embodiment of FIGS. 3 and 3A along with an optional reflector implement, and FIG. 5 shows yet another modified version of the asymmetrical-type embodiment of FIGS. 3 and 3A.

Figure 6B:
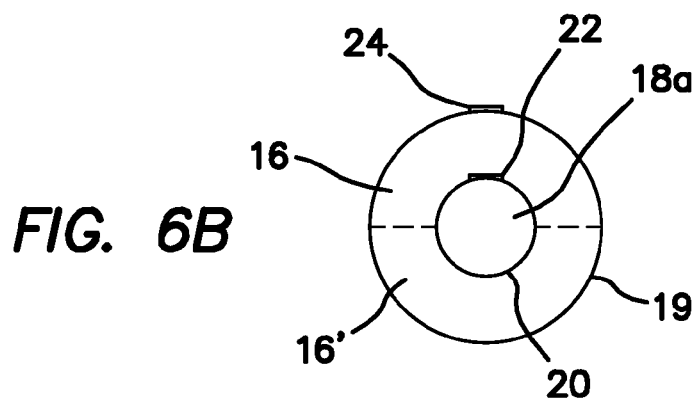
FIG. 6B shows an end cross-sectional view of the transverse-pumping arrangement.

According to a side-pumped or transverse-pumped implementation such as depicted in FIG. 6, components may be provided, for example, as one or more optic pairs (e.g., each pair being formed of a High Reflector HR and/or an Output Coupler OC) at different vicinities (e.g., at, on, or near an exterior surface 19 and an interior surface 20) of the active media 16, whereby the components of each optical pair are separated, for instance, by a distance t3 as measured along a radial direction. As with the above-described implementations (cf. FIGS. 1-5), the arrangement and features of FIG. 6 may be embody any combination or permutation, and/or modifications thereof of those described herein. Circular perimeters of the HRs and/or OCs as illustrated in FIG. 6A, for instance, can provide a benefit of enabling coupling to fibers. FIG. 6A shows a top plan view of the transverse-pumping arrangement, and FIG. 6B shows an end cross-sectional view of the transverse-pumping arrangement. Part or all of the inactive media 16' may alternatively comprise an active media 16 and/or HR and OC elements may be disposed thereon or thereabout.

Regarding the mentioned donut-shaped radiation patterns mentioned above, in the context of one of many features of the present invention, such phenomena can be implemented to project an annular (e.g., ring-shaped) image (e.g., treatment beam) in proximity to (e.g., adjacent to and/or onto), a target, such as for example, a hard or soft tissue target, such as a tooth. Other examples of the present invention can project oval-shaped or rectangular-shaped images/beams, images/beams with other simple or complex shapes, and/or images/beams with other shape(s) adjacent to and/or onto a target, whereby a center of the projected image/beam contains less, a different amount and/or kind, or no, radiation.

In a typical hard-tissue embodiment, such as a dental hard-tissue cutting embodiment, a thickness of the annular beam projected to and/or onto the target can be about ½ mm (e.g., the ring can be about ½ mm thick). Here, the annular beam projected to and/or onto the target can have an outer diameter of about 1 mm and an inner (e.g., less or differently radiated, or non-radiated) diameter of about ½ mm. Put another way, the annular beam can contain an outer diameter of about a mm and can have a non-irradiated, concentrically-disposed center region having a diameter of about ½ mm.

A material tip can be provided in the middle (eg., in the center) of the projected beam of treatment energy. The material tip can be formed to protrude distally from an emitting end of the laser device (e.g. handpiece) for reasons including those set forth below. For one, the amount of protrusion of the tip can be set to space the emitting end of the handpiece from the target to provide a maximum power or other predetermined condition or effect (e.g., such as enabling or optimizing a cutting effect as described in U.S. Pat. No. 5,741,247) as explained below. In any event, the material tip can be formed of a material transparent to wavelength(s) of the handpiece, or not, depending on selected shapes, applications, energy profiles, etc. Typically, but not necessarily, the material tip is disposed in a radiation-free center of the beam (e.g., projected image) and thus can (but need not) be formed of a non-transparent material. Also, typically, but not by way of limitation, the material tip is designed and used as a target-contacting implement for providing, as examples, one or more of a means of tactile feedback to the user (e.g., to allow the user to better discern a location of the emitting end with respect to the target) and a means of breaking-up lased tissue or the island of tissue in the center of lased tissue.

A material tip can be in a shape of the tube or cannula, which can be either cylindrical in shape or tapered (ether way: tapered down to reduce diameter or tapered up to increase the diameter). This tube should be transparent for laser radiation and can be opened on both ends or closed at one or both ends. In case of closed cannula, there can be additional features to be introduced the central orifice: delivery of water or other liquid to the tissue, suction of the blood, other liquids or ablation by-products or creating vacuum to attach to the target tissue if operated in a closed areas.

A high power source of electromagnetic radiation according to the present invention has an interior (e.g., a housing, or a reflector, and/or pump cavity) with sidewalls that are shaped as (e.g., into), and which actually form, one or more radiation sources (e.g., light sources) that provide the driving energy (e.g., light) causing or resulting in the source outputting radiation (i.e., electromagnetic energy) by one or more of an emitting, reflecting or channeling of the radiation away from the reflector. According to implementations in which the interior is formed by a housing, the housing can comprise a multi-purpose housing, meaning, for example, the housing can operate to fulfill at least partially the purposes of being a reflector, a pump chamber, one or more stimulation sources and/or a gain medium. In another implementation, the multi-purpose housing can operate as a reflector and a radiation source.

The multi-purpose housing is made of material highly transparent to electro-magnetic radiation emitted by the source or sources (e.g., the stimulation sources), has a high thermal conductivity and serves as a heat sink (c.f. below). As for the reflector purpose, a reflector structure for reflecting wavelengths of one or more of the sources can be formed in direct contact with an exterior sidewall of multi-purpose housing.

In typical implementations, the source comprises a reflector illuminator hybrid monoblock and/or outputs energy (e.g., coherent light) with an average power of 0.1 to 100 W, such as according to certain embodiments 0.1-10 W. Thus, although the invention is not limited to very large output powers, a feature of the present invention is the source is capable of outputting such relatively large powers.

In one aspect, a high power source of electro-magnetic radiation has a multi-purpose housing which comprises an interior filled with a material forming at least a light source and further comprises a reflector which can envelope (optionally) a laser rod surrounded by light sources for providing light excitation to the laser rod.

As an aid in describing the invention, for illustrative purposes only and not by way of any limitation, the following drawings and accompanying description are provided in the exemplary context of a medical laser device and a method of operating the medical laser device to perform surgical functions. Any content intended to cause the invention to be limited to such particulars, if at all, will be clearly and unambiguously demarcated as such.

An electromagnetic energy radiating (e.g., a laser, such as but not limited to a laser, such as a solid-state laser) system according to the invention comprises a gain medium (e.g., laser rod) for outputting electromagnetic energy (e.g., coherent light) and one or more stimulation sources (e.g., flashlamps and/or diodes) disposed in proximity thereto for emitting driving (e.g., pumping) energy toward the gain medium causing the gain medium to output the energy. Flashlamps, when used as the stimulation sources herein, are driven by flashlamp currents. The flashlamp currents drive the flashlamps to thereby produce and emit the driving energy (e.g., flashlamp light), which in turn is directed to the gain medium (e.g., laser rod) both directly and by aid of a reflector. The driving energy emissions (e.g., light distributions), as generated by the stimulation sources and modified/directed by the reflector, drive the gain medium to produce the output energy (e.g., coherent light).

The gain medium and stimulation sources are disposed within the reflector, which can take the form of a chamber (e.g., a pump-chamber reflector), for example, that directs the driving energy emitted from the stimulation sources toward the gain medium. The reflector can comprise one or more of a diffuse (e.g., ceramic construct with highly uniform distribution of energy) and a specular (e.g., reflective coating with high efficiency and less uniformity) structure, property and/or function.

In addition to directing driving energy from the stimulation sources into the gain medium, the reflector further can optionally provide cooling to one or more of the gain medium and the stimulation sources. According to a feature of the invention, the reflector comprises cooling structure for providing fluid, such as but not limited to non-liquid (e.g., gas) cooling fluid, to one or more of the gain medium and the stimulation sources. That is, the cooling can be by way of convection through solid materials which, ultimately, are coupled to a fluid-cooled heat sink (e.g., a heat sink externally disposed relative to the reflector).

A feature of the invention seeks to reduce distortion (e.g., thermal distortion, e.g., from thermal wedging) by disposing the stimulation source in parallel fashion relative to the gain medium. Nonetheless, to the extent thermal distortion, such as from a thermal gradient along or transverse to an axis of the gain medium, may still exist (e.g., creating internal stresses in the gain medium, shortening the lifetime, and/or reducing efficiency), a further feature of the invention seeks further to reduce the distortion by disposing a plurality (e.g., two) stimulation sources in parallel fashion on opposing sides of the gain medium. Accordingly, greater stimulation (e.g., pumping) may be implemented with less thermal distortion (e.g., curving of the gain medium), especially in an exemplary context of gas cooling.

Another feature of the invention comprises forming the interior volume of the reflector of a material (e.g., not a gas) that has a high thermal conductivity (e.g., greater than that of air) and that is transparent to wavelength(s) of the driving energies from the stimulation sources. The material can have a thermal conductivity that is greater than air, e.g., such as that of sapphire. At a temperature of about 25° C., the thermal conductivity of air may be about 0.024 W/m° C., whereas that of sapphire may be about 23.0 W/m° C. A few other materials, provided for reference only and not as having any particular suitability for use with the present invention, are foamed plastics (for insulation materials), fiberglass, glass and granite, having thermal conductivities of about 0.03, 0.04, 1.05, 1.7-4, respectively, at about the same temperature. An aspect of the current invention can be to form the interior volume of the reflector of a material having a thermal conductivity (measured at 25° C.) at least as large as or larger than a thermal conductivity, which is about 50% greater than that of air (e.g., in the example, if air is 0.024 then the thermal conductivity would be about 0.036), or, more preferably, that is about 0.03 W/m° C., or 0.04 W/m° C. or, more preferably, that is greater than about 1.0 W/m° C., or, even more preferably, that is greater than about 4.0 W/m° C.

According to a typical embodiment, the interior of the reflector is solid or gelatinous; rather than gaseous, and/or is filled with (e.g., contains) a stimulation-source encasing material such as that typically used for the casing material of a stimulation source (e.g., a flashlamp).

One aspect of the invention forms the interior of the reflector with a stimulation-source encasing material, or a functional analogy or equivalent thereof, that contacts the encasing material of the stimulation sources (e.g., which are held within respective cavities, or lumens, of the reflector). According to one aspect, no gaps (e.g., no channels and/or fluid passages) exist (e.g., are disposed or formed) between each of the stimulation source(s) and the interior of the reflector. Another aspect of the invention integrally forms the interior (e.g., the solid interior) of the reflector with the encasing material of the stimulation sources. Yet another aspect of the invention integrally forms the interior of the reflector with (e.g., of, or as) the same material as that of one or more of the stimulation sources, whereby parts (e.g., outer surfaces) of the stimulation sources can be considered as actually forming the interior of the reflector or, in other words, the interior of the reflector can be considered to actually form (e.g., make up, or define) the stimulation sources (e.g., the outer surfaces of the stimulation sources). Thus, material (e.g., solid material having high thermal conductivity and/or optically transparency to the wavelengths of the driving energy), such as encasing material, can define (e.g., form) the interior (e.g., the interior sidewall) of the reflector (e.g., the pumping chamber) and can also define (e.g., form) the exterior surfaces of one or more of the stimulation sources.

Figure 7:
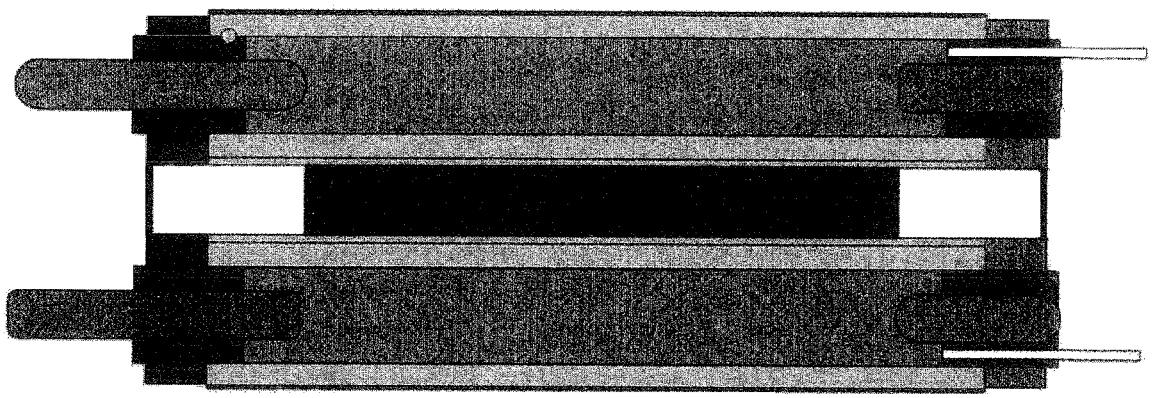
FIG. 7 shows a side cross-sectional view of a chamber (e.g., reflector) according to an embodiment of the present invention.
Figure 8:
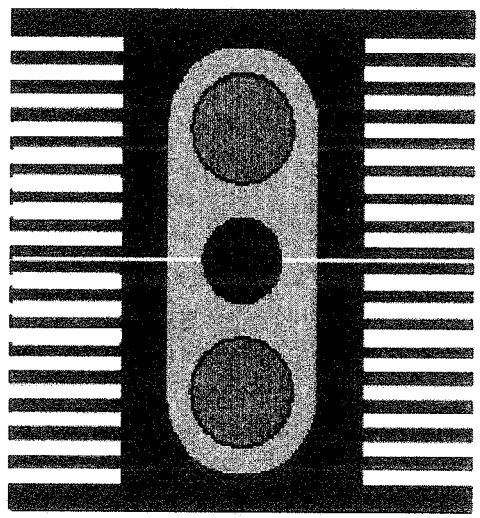
FIG. 8 shows an end cross-sectional view of the same embodiment.

Referring more particularly to the drawings, FIG. 7 shows a side cross-sectional view of a reflector according to an embodiment of the present invention, and FIG. 8 shows an end cross-sectional view of the same reflector. A particular implementation of the last-mentioned aspect (i.e., of integral formation) forms the interior of the reflector out of the stimulation-source encasings. As depicted in the drawings, material of the reflector thus can be extended to fill the interior thereof and, further, can have inner surfaces defining the cavities (e.g., lumens) of the stimulation sources (e.g., actually making/forming the stimulation sources, so none need be inserted into the reflector but rather just anode/cathode/active media need be inserted into the cavities formed by the material) and an outer surface defining the outer surface of the reflector. In typical embodiments, the material (e.g., encasing material) comprises a material that is optically transparent to wavelength(s) of the stimulation sources and/or that has a high heat conductivity (e.g., at least greater than that of air). According to exemplary implementations, the stimulation sources comprise flashlamps (e.g., Lamp 1 and Lamp 2 of FIG. 7) and/or the encasing material comprises sapphire.

Figure 9:
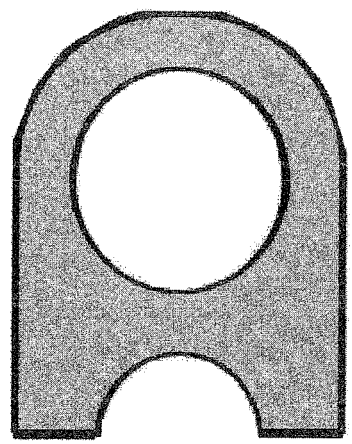
FIG. 9 shows an end cross-sectional view of a first flashlamp/reflector structure according to another embodiment of the invention.
Figure 10:
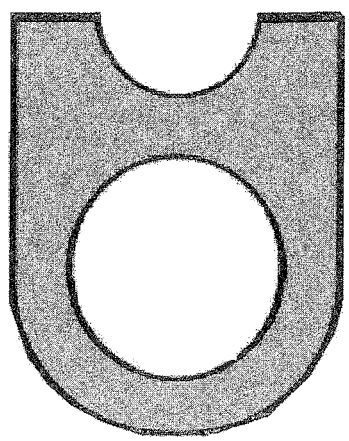
FIG. 10 shows an end cross-sectional view of a second flashlamp/reflector structure according to the other embodiment.
Figure 11:
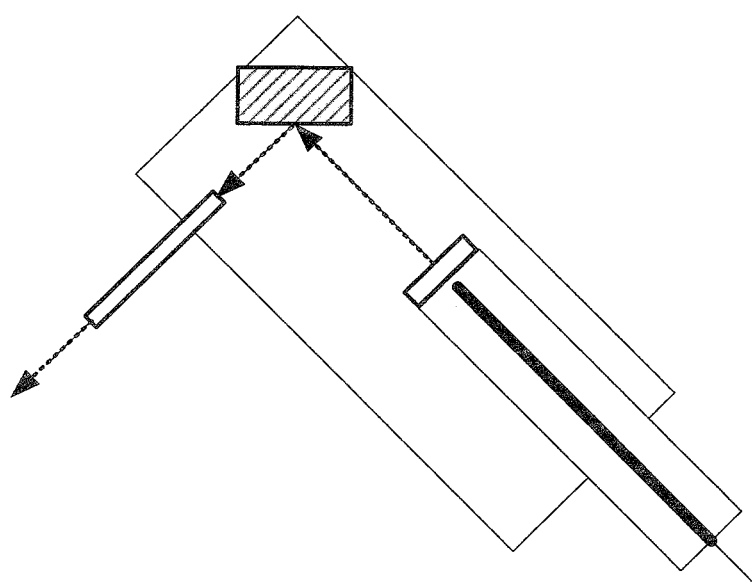
Figure 12:
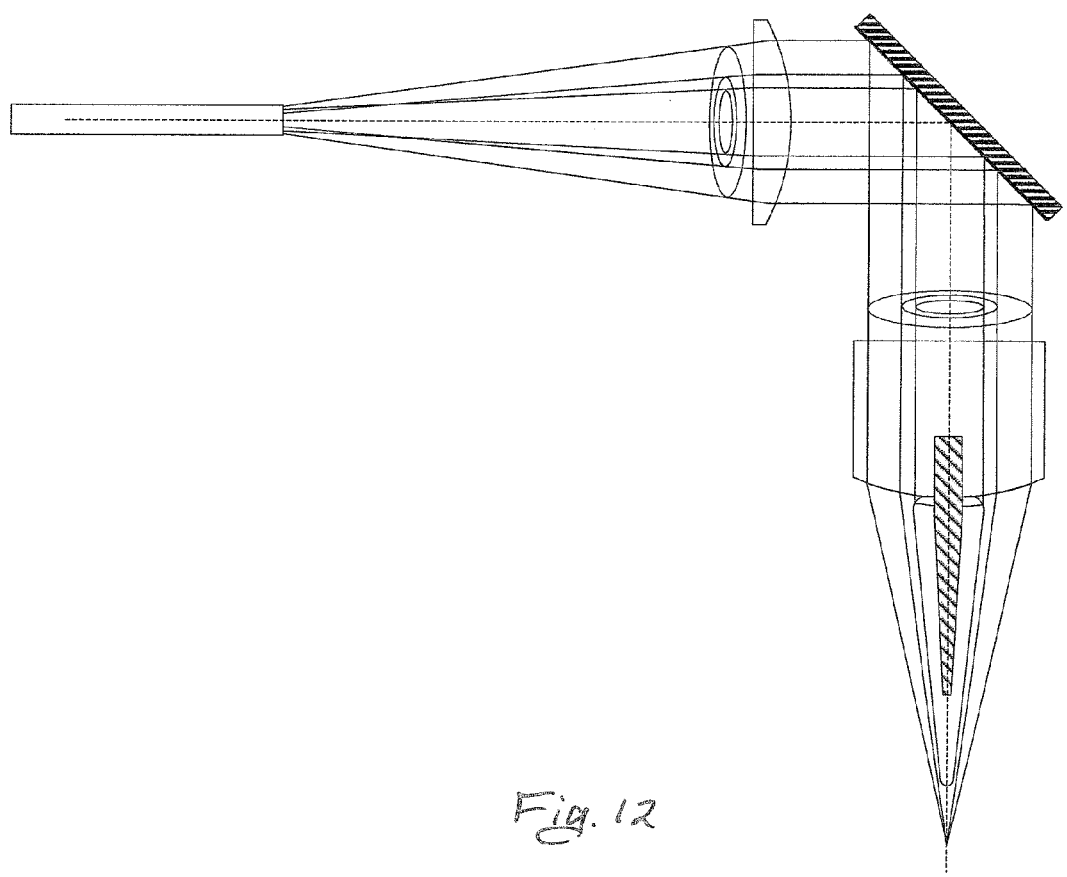
Figures 13A, 13B:
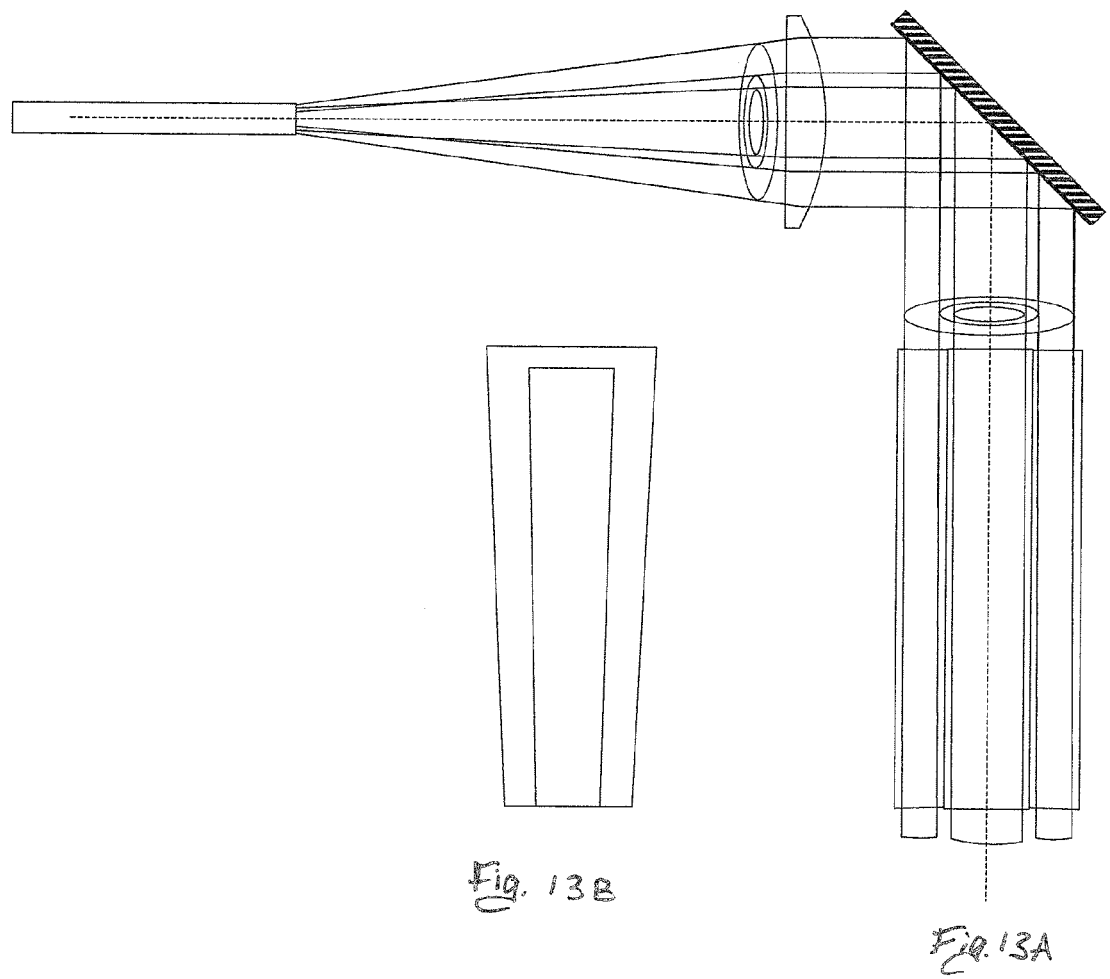
Figure 14:
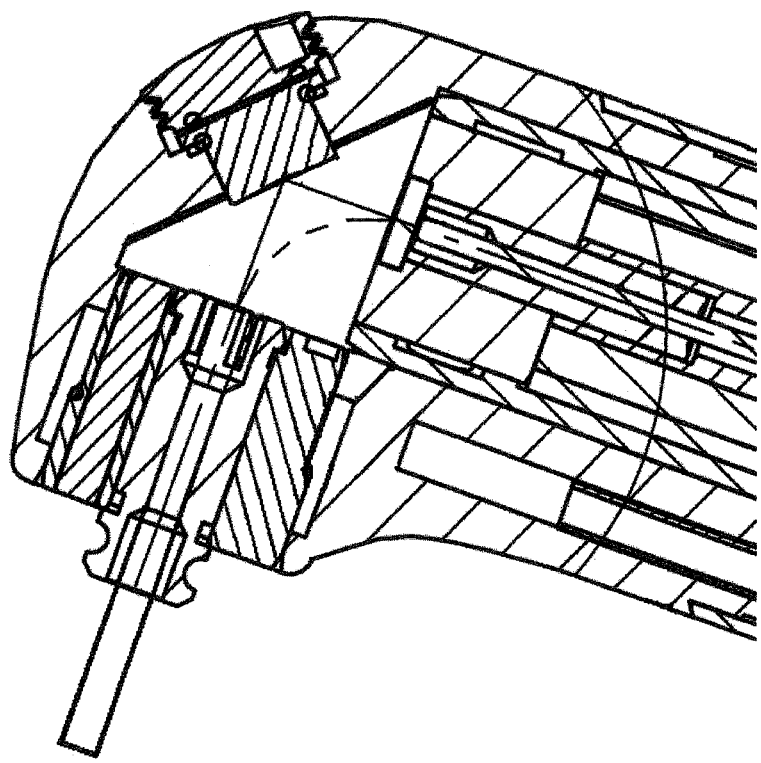
Figure 16:
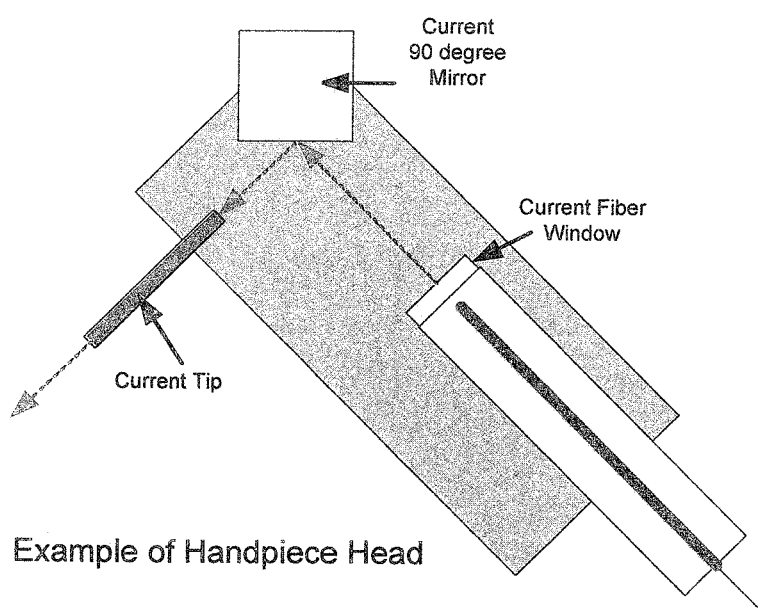
Figure 17:
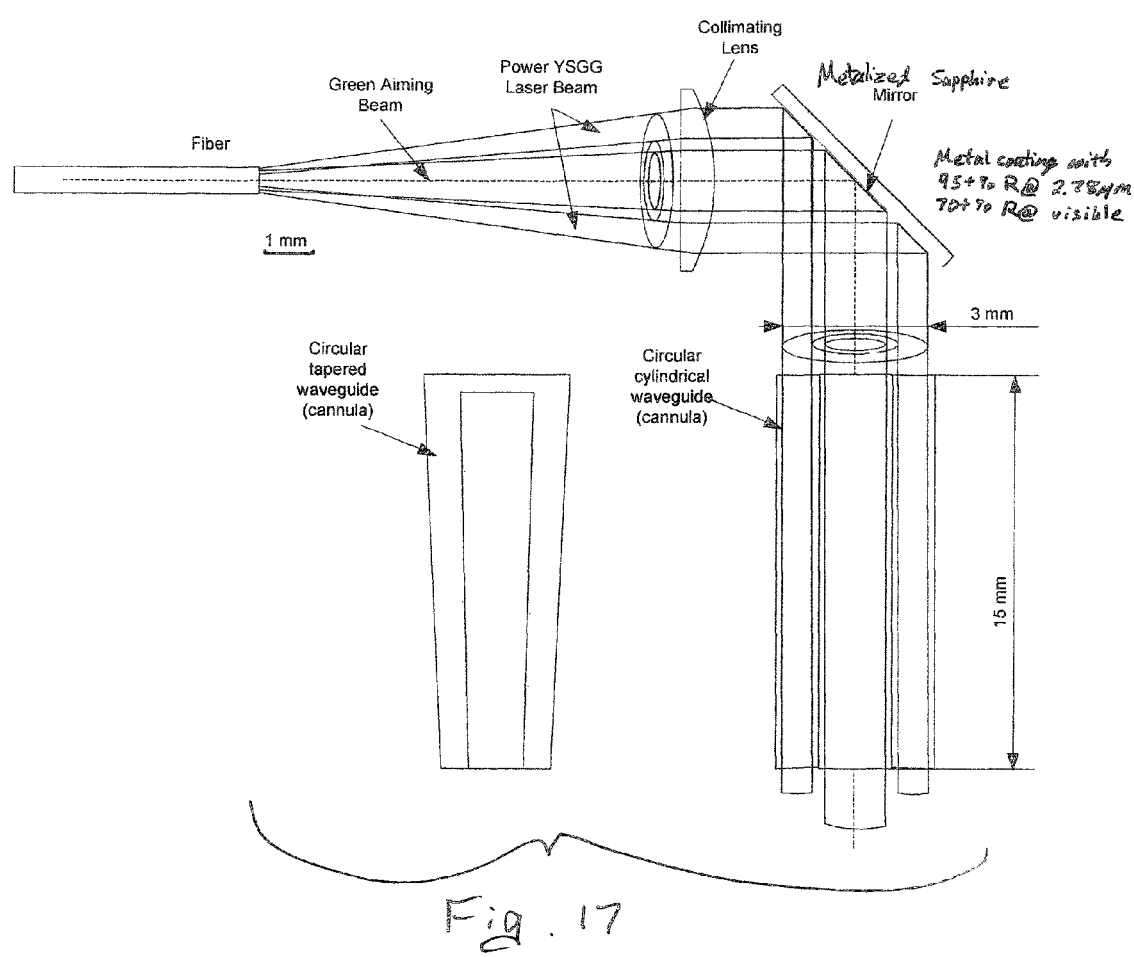

FIG. 9 shows an end cross-sectional view of a first flashlamp/reflector structure according to an embodiment of the invention, and FIG. 10 shows an end cross-sectional view of a second flashlamp/reflector structure according to the other embodiment. Here, the interior of the reflector is formed out of the stimulation-source encasings, whereby the encasings of the stimulation sources are expanded to such an extent as to fill the interior of the reflector. According to this aspect of the invention, integral formation of the reflector with (e.g., of, as, or out of) the same material as that of one or more of the stimulation sources may combat, reduce or stabilize thermal distortion, such as from a thermal gradient along or transverse to an axis of the stimulation source, which may exist (e.g., creating internal stresses in the stimulation source operating potentially to shorten lifetime and/or reduce efficiency thereof) under certain circumstances or operating conditions. As a consequence of this arrangement, greater stimulation may be implemented, such as in an exemplary context of gas cooling.

In FIGS. 9 and 10, along the context of encasings of the stimulation sources being expanded to form the reflector, each encasing of each stimulation source is expanded to form half of the reflector. The two halves, e.g., that of FIG. 9 and that of FIG. 10, can then be secured together using any means that would be deemed appropriate to one skilled in the art, to form the reflector. For instance, the two halves may be secured using clamps, bands, any type of vice-grip structure, a press or a press fit, welding, bonding, gluing, complementary or other types of housing/aligning/holding structures, hinges, flange structures, and combinations thereof, as would be apparent to one skilled in the art in view of this disclosure. In typical implementations, stimulation sources are not inserted into the cavities of the upper and lower halves as each of the halves, in and of itself, forms the body of a stimulation source (e.g., thus having an anode and cathode at opposing ends thereof, and a suitable gas (e.g., Xenon) or other stimulation therein, appropriate coatings, suitable dimensions, etc). Furthermore, according to some (e.g., alternative) embodiments, one or more structures (e.g., one or more stimulation source(s) and/or any one or more of the fluid or air cooling structures/functions such as the "air cooling chamber," "air path," "flow tube," "air flow tubes," and "transparent reflector block") of the above-referenced Prov. App. 61/221,544 may be included, in whole or in part, in any combination, with any of the aspects, features and structures described herein.

An optional gain medium can comprise a solid material provided in the form of an elongated cylindrical rod having a length, for example, from about 50-70 mm and a diameter, for example, of about 3-4 mm. For greater cooling, the cylindrical rod can be provided with a greater length and/or a relatively high length-to-diameter ratio. For instance, the gain medium can range from the above length up to about 110-130 mm and/or have a diameter ranging from about 2-6 mm. Exemplary constructions according to the invention can be about 110-115 mm long by about 3-4 mm (e.g., about 3 mm) wide. Such an elongate gain medium, while providing heat dissipation advantages, may be more susceptible to thermal distortion, such as in an exemplary context of air cooling, thereby potentially enhancing an importance or usefulness of the multiple, parallel-disposed stimulation sources, which may be formed (by way of preference rather than limitation) with lengths close to or matching that of the gain medium.

As shown, the elongate gain medium can comprise a suitable active material, such as a crystalline material (e.g., a glass or a plastic) doped with an active ion. According to one aspect, no gaps (e.g., no channels and/or fluid passages) exist (e.g., are disposed or formed) between the gain medium and the interior of the reflector. Other implementations, however, may comprise one or more gaps (e.g., channels, gaps and/or fluid passages) disposed or formed between the gain medium and the interior of the reflector.

As presently embodied, the active material is formed in, or as a part of, or is, a resonator. In exemplary constructions, the resonator may be embodied (e.g., defined) by a pair of reflecting elements (e.g., mirrors). The reflecting elements may be disposed at opposing ends of the active material. For instance, one or both of the reflecting elements may be spaced from, attached to (using known techniques), and/or formed as a coating on (using known techniques), a respective end of the active material. The arrangement illustrated in FIG. 7 comprises two reflecting elements formed as attached structures within the reflector.

With particular reference to FIG. 7, the two reflecting elements are shown attached to opposing ends of the active material. According to the depicted assembly, each of the reflecting elements is coupled to the active material by way of attachment to (e.g., being coated and/or formed on) an end of an inactive material (e.g., an undoped YSGG glass), which in turn is attached (e.g., press fit, contacted, and/or bonded) to the active material (e.g., an Er,Cr:YAGG doped glass rod). In other implementations, the lengths of the active material and/or the inactive material portions may be different. For example, such length(s) may be different with the net length of all three portions still being about the same to dispose the two reflecting elements in a position as shown flush with sidewalls/sides of the reflector. In other embodiments, the two reflecting elements are not flush.

In alternative embodiments/structures, one or more of the reflecting elements can be detached from (e.g., not formed as coatings on and/or wholly or partially free standing relative to) the active material and/or disposed outside of the resonator (e.g., yet still aligned along the optical axis of the active material). In other embodiments, lengths of one or more of the inactive material portions are zero and/or the two reflecting elements are formed to be flush, or not flush, with sides of the reflector. The two reflecting elements may comprise, for instance, a collector, e.g., in the form of an output coupler (OC), and a high reflector (HR). In laser embodiments, such as in the context of, but not limited to, those (e.g., solid state) lasers in which the gain medium is a laser rod that is pumped by stimulation sources comprising flashlamps to cause the laser rod to reach active states and provide laser gain upon exposure to light from the flashlamps, the OC and HR elements can comprise high reflectivities. In typical embodiments, the OC can comprise a reflectivity ranging from low to high values, and the HR can comprise a mirror (e.g., with a very high reflectivity). Particular implementations may comprise the OC having reflectivities ranging from 6 to 99%, or from 70 to 95%, or of about 80%, and the HR having a reflectivity of 99%, or 99.5%, or 99.9%.

One or more of the optional inactive material(s), the reflecting element(s), and the active material may be contacted with an immersive media (e.g., an adhesive with high thermal conductivity and optical transparency to wavelength(s) of the stimulation sources). For instance, the immersive media may consist of, consist essentially of, or comprise, one or more of water, a gel (e.g., viscous glycerine), and an adhesive (e.g., polymethyl methacrylate loaded with a suitable powder). In one example, the immersive media is water. In another example, the immersive media is disposed between the gain medium and the material (e.g., sapphire) of the reflector interior. The material of the reflector interior can form a lumen or cavity for holding the gain media, whereby, for example, the immersive media may be disposed within the lumen or cavity along with the gain media. Another example may comprise the immersive media in the form of a water-based gel which is optically transparent to the wavelength(s) of the stimulation sources and which has a high heat conductivity (e.g., much greater than that of air) disposed between the gain medium and the material (e.g., sapphire) of the interior of the reflector.

The exterior of the reflector (e.g., sapphire) can comprise surfaces (e.g., highly polished surfaces) that are coated (i.e., with a high-reflectivity material) to enhance the reflectivity of the driving energy (e.g., pump light) from the stimulation sources. The reflector generally will be formed to have a well defined shape suited to provide a high energy-transfer efficiency. A non-limiting range of reflector outer diameter (OD) values can be from about 12 mm to about 55 mm, and an exemplary, non-limiting range of reflector values can be about 10 mm length to 150 mm. In the case of flashlamp pumping of a gain medium in the form of a laser rod, whereby the flashlamp energy is directed into the laser rod in such a manner that it is concentrated to stimulate the laser rod, such flashlamps can be used as stimulation sources for an Erbium laser system, for example, driven by flashlamp currents comprising predetermined pulse shapes and frequencies.

The reflector interior may comprise, in alternative implementations, one or more of series or parallel cooling paths, energy absorbing flow tubes, crystal and lamp water jackets, coolant fittings, and O-rings. Typically, the reflector of the invention comprises an elliptical or cylindrical shape surrounding the stimulation sources and the gain medium. Part or all of the reflector (e.g., parts radially exterior to the encasing material) in exemplary (e.g., additional and/or alternative) constructions may comprise a cylindrically- or elliptically-shaped body formed to comprise, in part or in while, in combination with the encasing material (e.g., sapphire) or not, a stainless (e.g., gold, silver, aluminum, stainless steel, or bronze) or a non-metallic (e.g., ceramic or doped glass) material. According to certain implementations, to facilitate the stimulation sources' purpose of generating driving energy distributions for driving the gain medium, reflective surfaces can comprise any of the aforementioned items and/or be disposed in close proximity to one or more of the stimulation sources and the gain medium. Such reflective surface configurations, which may be referred to as reflectors, can be formed, for example, on one or more of the driving-energy exposed surfaces of the interior (e.g., chamber) of the reflector.

Any part or all of the gain medium may be formed (e.g., integrally formed) as part of the reflector. For example, part or all of an encasing of the gain medium can be expanded to form part (e.g., a part, or even much/most/all of a solid interior) of the reflector. In certain implementations, the interior of the reflector is formed out of or with the gain medium encasing, whereby the encasing of the gain medium and/or stimulation source(s) are expanded to such an extent as to fill the interior of the reflector. In other implementations, the interior of the reflector is formed out of one or more of the stimulation source encasing(s) and/or of the gain medium encasing. The interior volume of the reflector can comprise, for instance, a solid (e.g., sapphire) possessing a transparency to stimulation wavelength(s) and a high thermal conductivity. The material of the gain medium thus can be extended to fill part/all of the reflector interior of and, further, can have an inner surface defining a cavity of the gain medium (e.g., actually making/forming the gain medium, so a gain medium need not be inserted into the reflector but rather just HR, OC, active material, optional inactive material, etc., need be inserted/incorporated into/with the cavity formed by the material) and an outer surface defining the outer surface of the reflector. For instance, one or more of the two reflecting surfaces (e.g., HR and/or OC) may be coupled to the active material by way of being formed over an end of an inactive material (e.g., an undoped YSGG glass).

A feature of the present invention comprises the coating (e.g., by spray, dip, paint, deposition, vacuum, etc.) the outside (i.e., exterior) surface of the reflector with a high-reflectivity material, which may comprise, for example, gold, silver, or other high-reflectivity material (e.g., including any of the aforementioned items). A typical construction can comprise all, or substantially all, of the outside (i.e., exterior) surfaces of a pump chamber reflector being coated with the high-reflectivity material. According to an aspect of the present invention, the high-reflectivity material coat can be applied to the outside surface of a multi-purpose housing (e.g., reflector) using any material and/or process, in whole or in part, in any combination or permutation, that is known to be used for forming a high-reflectivity material on, for instance, a specular pump chamber reflector. As an example, a high-reflectivity material may be formed on the outer surface of a pump chamber reflector by vacuum deposition or electrolytic coating, of, for instance, silver onto the outer surface of the reflector (e.g., pump chamber reflector). In other embodiments, the diffusive pump chamber reflector may comprise a material, such as pyrex, quartz and/or the mentioned sapphire, formed into an elliptical (e.g., elliptical, cylindrical and/or solid tube) shape, the outside (i.e., exterior) surface of which is coated with a high-reflectivity material, as described.

The high-reflectivity material (e.g., coating) can have a thickness within a range of, for example, about 10 nm to about 10,000 nm, and in a particular example, of about 1000 nm. According to one implementation, a uniform coating thickness is provided over the entire multi-purpose housing, chamber or cavity (e.g., tube) outer surface. Following coating of the outer surface with a high-reflectivity material (e.g., silver), a protective layer may be formed over the high-reflectivity material. For example, the protective layer may comprise an anti-corrosive material, such as a silicon dioxide layer formed to, as just one of many examples, a thickness of about 1 micron.

Fluid (e.g., air) can be circulated over and/or around the reflector to provide cooling. According to one feature, circulation of a fluid (e.g., gas) can comprise pre-cooling thereof, e.g., at a gas intake, so the assembly can have a greater temperature range for the gas to be heated and, therefore, remove more thermal power from the elements. A key can be to optimize efficiency, whereby all benefits gained from having fluid (e.g., air) cooling are not lost (e.g., complexity, cost and size of the cooling system) but rather are compounded.

According to a feature of the present invention, a heat sink is disposed on the exterior of, or otherwise coupled to, the reflector. It may be formed, for example, on part or all of the exposed/outside surfaces of the reflector following placement of the high-reflectivity material and/or following coating of the protective layer. As presently embodied, the heat sink can comprise a material referred to as "carbon foam." That material can be machined, enforced, and yet has better heat-exchanging capabilities in air than aluminum foils within water. An example of the material is POCOFoam® by Poco Graphite, Inc. of Decatur, Tex. Enforcement of the carbon foam air flow does not erode that material when blowing through (like red rocks in Arizona . . . ). Enforcement can comprise depositing a few angstroms (several molecular layers) of ceramic film over the surface area of the carbon foam (e.g., which foam may be about 70% porous). Information on the carbon foam, which is incorporated herein by reference, can be obtained at http://www.ornl.gov/info/ornlreview/v33_3_00/foam.htm and http://www.ms.ornl.gov/researchgroups/CMT/FOAM/foams.htm. The heat sink can comprise ribs, as depicted in FIG. 8 and known to those skilled in the art of heat sinks Air thus can be circulated over, around and through protuberances and channels of the heat sink for cooling. One side of the heat sink can be mounted to the cold plate of the Thermo-Electric Cooling device, for greater cooling.

According to certain implementations, laser energy generated by the reflector is output from a power or treatment fiber, and is directed, for example, into fluid (e.g., an air and/or water spray or an atomized distribution of fluid particles from a water connection and/or a spray connection near an output end of the handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

FIGS. 11-18 show further aspects of the present invention.

By way of the disclosure herein, a laser has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of the treatment radiation and/or of the fluid from the fluid output or outputs.

Corresponding or related structure and methods described in the following patents assigned to Biolase Technology, Inc. are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device; U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S.

Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled Multiple fiber-type tissue treatment device and related method; App. Pub. 20080212624 entitled Dual pulse-width medical laser; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142743 entitled Medical laser having controlled-temperature and sterilized fluid output; App. Pub. 20060099548 entitled Caries detection using timing differentials between excitation and return pulses; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

Regarding the material tip, a feature of the present invention can be to maintain a bounded layer of fluid particles, which is not too thick and which is not too thin. A fiber optic tip (e.g., the material tip and/or the emitting end) placed into (e.g., and/or placing treatment energy into) a distribution of fluid particles and, additionally, placed in close proximity (2-3 mm, for example) of a target surface, creates a thin layer of fluid particles between the incident treatment (e.g., concentrated electromagnetic) energy and the target surface. Other distances are possible within the scope of the present invention, depending on, for example, the selected laser intensity and wavelength, the selected fluid (if any), and the selected distribution of atomized fluid particles (if any). An electromagnetically induced cutter can comprise a laser, microprocessor and user interface. The electromagnetically induced cutter further can comprise an air and/or water source for supplying one or more atomization nozzles with air and/or water.

In accordance with an embodiment, one or more material tips (e.g., contacting arms) may be used, taking on basically any form so long as the one or more contacting arms provide a function of spacing the source of electromagnetic energy from the target surface. For example, in one embodiment, the one or more contacting arms may be constructed to contact another surface, such as another part of the patient besides the actual target or a peripheral part of the target, while still providing the function of spacing the source of electromagnetic energy from the target. In other modified embodiments, one or more additional tissue contacting arms may be implemented besides just one. For example, three or more tissue contacting arms may be disposed at, for example, about 120 degrees, 240 degrees and 360 degrees. In another embodiment, the tissue contacting arm or arms are part of and form at least a partial enclosure, such as a hemispherical enclosure. In yet another embodiment, the tissue contacting arm(s) form at least a partial cylindrical, rectangular or other enclosure. The contacting surface of the enclosure (i.e., the surface that contacts the target surface) may thus comprise one or more points for touching the target surface (corresponding to one or more contacting legs), or may comprise a circular, oval, rectangular or other continuous or non-continuous perimeter for touching the target surface.

For example, the contacting arms may form an oval, hemispherical enclosure, such as that of an upside down spoon, wherein the contacting surface of the oval, hemispherical enclosure forms an oval shape or edge for touching the target surface. Thus, in use, an oval shape on the target surface would be enclosed by the oval, hemispherical configuration. As used herein, the term "hemispherical" is not intended to define half of a sphere but, rather, to define any closed surface with an opening for contacting the target surface. Thus, in an embodiment wherein the hemispherical configuration forms a rectangular edge for contacting the target surface, the enclosure may have any of a variety of shapes such as for example half or a sphere that transitions into the rectangular edge, or an open ended cubical enclosure with the rectangular edge. The distal ends of the tissue contacting arms are preferably rounded or smooth-surfaced to allow the tissue contacting arms to glide over the target surface, such as a patient's tissue, tissue, crystal or glass. In one modified embodiment, at least one of the distal ends comprises a ball roller.

A moisture output can direct moist air and/or water or an atomized air/water mist/spray into the path of the electromagnetic energy. Water from the moisture output can help to allow the tissue contacting arm(s) to slide over the target. In one embodiment, water or another fluid, or an additive to water, having lubricating properties, may be emitted from the moisture output. For example, soft water may be emitted from the moisture output. The moisture output can comprise an atomizer for outputting atomized fluid particles into the path of the electromagnetic energy above or on the target surface. A suction can removes excess moist air and/or atomized fluid particles. The suction can be disposed to facilitate a fluid flow path from the moisture output 90, through the interaction zone, and out through the suction.

Any of the tissue contacting arm(s) herein may be formed of stainless steel or a plastic, for example; part or all of the tissue contacting arms may be formed of a transparent material, such as a transparent plastic.

Tissue contacting arm(s) can be in a shape of a tube, cylindrical or tapered and utilize center opening for clinically functional operations: delivery or suction of fluids, suction of ablation products or attaching to the operating site by vacuum suction.

At least one of the tissue contacting arms can comprise a proximal end, a distal end, and a suction passageway extending therebetween. Each suction passageway can be constructed to carry surplus fluids and debris from the target surface. In order to facilitate this end, one or more of the rounded surfaces (e.g., ball rollers) at the distal ends may be configured to have a smaller or flatter profile to place the relative position(s) of the suction passageway opening(s) closer to the target surface. In one embodiment, the opening or openings of the suction passageway(s) may be placed within the rounded surface(s) or ball roller(s) at the distal end(s). Each suction passageway can, for example, remove water particles that have been emitted and carry them proximally through the suction passageway and out of the handpiece. The air and water lines may be configured to output, soft water or another fluid, or an additive to water, having lubricating properties. One or more atomizers, mist generators, or moist air outputs (fluid outputs) may be disposed in, connected to or fitted between the tissue contacting arms 212.

All of the contents of the preceding published applications are incorporated herein by reference in their entireties. Although the disclosure herein refers to certain illustrated embodiments, it is to be understood that these embodiments have been presented by way of example rather than limitation. For example, any of the radiation outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. A high power source of radiation, comprising:
   a gain medium comprising a material;
   a cavity formed of the material;
   a radiation source surrounded by the gain medium and disposed within the cavity, the radiation source comprising a gas which is capable of forming an arc discharge operable as a source of pumping within the cavity and being configured to emit energy responsive to the pumping for interception by the surrounding gain medium;

a sidewall of the cavity, wherein the sidewall of the cavity is formed by the material, and wherein the sidewall of the material directly contains the gas;

wherein the energy comprises driving energy that causes the gain medium to output amplified electromagnetic energy.

2. The high power source as set forth in claim 1, wherein: the amplified electromagnetic energy comprises an outer region surrounding an inner region of less radiation.

3. The high power source as set forth in claim 1, wherein: the high power source further comprises a heat dissipater enveloping part or all of the material.

4. The high power source as set forth in claim 1, wherein: the high power source further comprises a heat dissipater removably attached to the material and adapted to carry away heat generated within the material.

5. The high power source as set forth in claim 1, wherein the radiation source is configured to emit electromagnetic radiation within the cavity inside the material.

6. The high power source as set forth in claim 1, wherein a collector is in the form of at least one output coupler (OC) and at least one high reflector (HR).

7. The high power source as set forth in claim 2, further comprising a material tip which during use is disposed in the inner region.

8. The high power source as set forth in claim 7, wherein the material tip comprises one or more of a tube, a cannula and a cylindrical shape.

9. The high power source as set forth in claim 7, wherein a shape of the material tip comprises a taper.

10. The high power source as set forth in claim 7, wherein the material tip is transparent to the amplified electromagnetic energy.

11. The high power source as set forth in claim 7, the material tip comprising a cannula having two opposing ends one or both of which is closed.

12. The high power source as set forth in claim 11, further comprising at least one output structured to apply one or more of liquid and suction to the inner region.

13. The high power source as set forth in claim 11, further comprising at least one output structured to apply suction to the inner region thereby to create a vacuum for attachment of the material tip to a target tissue.

14. The high power source as set forth in claim 7, wherein the material tip comprises a cannula with two opposing open ends.

15. The high power source as set forth in claim 7, further comprising a tissue contacting arm.

16. The high power source as set forth in claim 15, wherein: the tissue contacting arm comprises a center opening for clinically functional operations including one or more of delivery or removal of fluids, suction of ablation products and attachment to an operating site by vacuum suction; and the material tip comprises another tissue contacting arm.

17. A high power source of radiation, comprising:
a gain medium comprising a material, a cavity being formed within the material;
a radiation source positioned within the material, wherein the radiation source includes a liquid or gas that is directly contained by the material of the gain medium, and wherein the radiation source emits energy that is received and amplified by the material of the gain medium;
a wave guide configured to direct the amplified energy from the gain medium to an electromagnetic energy output; and
a tissue contacting arm connected to the source of radiation near the electromagnetic energy output, the tissue contacting arm being configured to maintain a particular spacing between the electromagnetic energy output and a treatment site.

18. The high power source of radiation of claim 17, wherein the contacting arm includes a moisture output for introducing a liquid at or near the target.

19. The high power source of radiation of claim 17, wherein the contacting arm is configured to enclose the target.

20. The high power source of radiation of claim 17, wherein the contacting arm is configured to touch a surface that is outside of the target, at a periphery of the target, or at the center of the target.

* * * * *